United States Patent [19]

Campbell et al.

[11] Patent Number: 4,525,704
[45] Date of Patent: Jun. 25, 1985

[54] ENZYMATIC TOXIC GAS SENSOR

[75] Inventors: Donald N. Campbell, Timonium; John C. Schmidt, Baltimore, both of Md.

[73] Assignee: Allied Corporation, Morristown, N.J.

[21] Appl. No.: 550,272

[22] Filed: Nov. 9, 1983

[51] Int. Cl.³ .................... G08B 17/10; C12Q 1/00
[52] U.S. Cl. .............................. 340/632; 204/403; 204/412; 204/415; 435/291; 435/817
[58] Field of Search .............. 204/1 T, 1 E, 402, 403, 204/412, 415; 435/291, 287, 817, 20, 18; 340/632

[56] References Cited
U.S. PATENT DOCUMENTS

| | | | |
|---|---|---|---|
| 3,642,600 | 2/1972 | Seiger et al. | 204/403 |
| 4,132,616 | 1/1979 | Tantram et al. | 204/415 |
| 4,284,719 | 8/1981 | Agerhem et al. | 435/18 |
| 4,324,632 | 4/1982 | Tantram et al. | 204/415 |
| 4,326,200 | 4/1982 | Bushman | 340/632 |
| 4,376,689 | 3/1983 | Nakamura et al. | 435/817 X |
| 4,406,770 | 9/1983 | Chan et al. | 204/412 X |
| 4,411,989 | 10/1983 | Grow | 435/291 X |

Primary Examiner—G. L. Kaplan
Assistant Examiner—Nam X. Nguyen
Attorney, Agent, or Firm—Robert M. Trepp; Bruce L. Lamb

[57] ABSTRACT

An enzymatic toxic gas sensor 10 having a plurality of parallel planar surfaces and a buffered electrolyte reservoir 44. The buffered electrolyte is conveyed by means of diffusion to a substrate 28 to dissolve the substrate. The substrate diffuses to an immobilized enzyme where it is hydrolyzed if the enzyme is active. An electrochemical cell continuously monitors the hydrolyzed substrate concentration which is an indication of the enzymatic activity and presence of toxic gas. A circuit means responds to the current output of the electrochemical cell to indicate the presence or absence of a toxic gas. The shelf life of the sensor is extended by means of a separator for maintaining the enzyme dry and inactive. The enzyme in the preferred embodiment is acetylcholinesterase (AcHe).

19 Claims, 4 Drawing Figures

U.S. Patent  Jun. 25, 1985  4,525,704
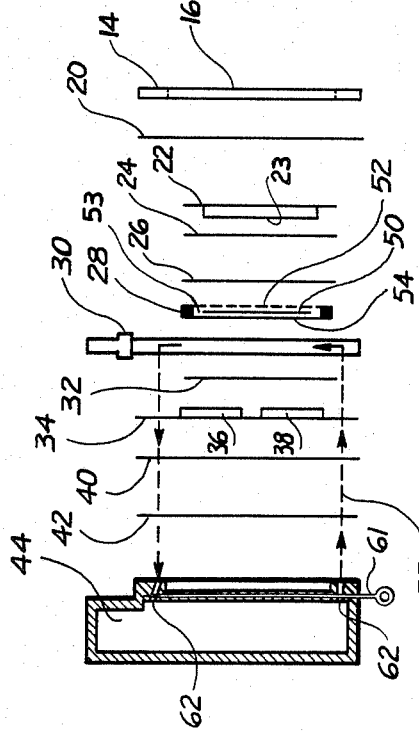
Fig·2
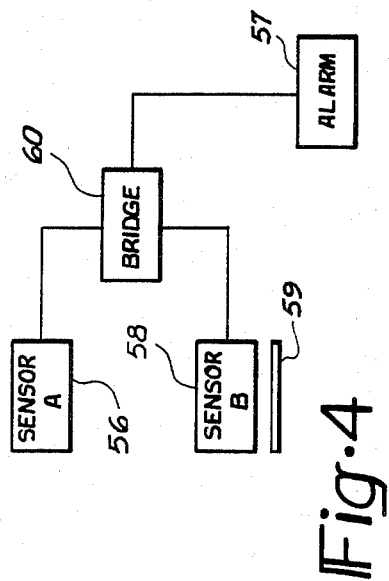
Fig·4
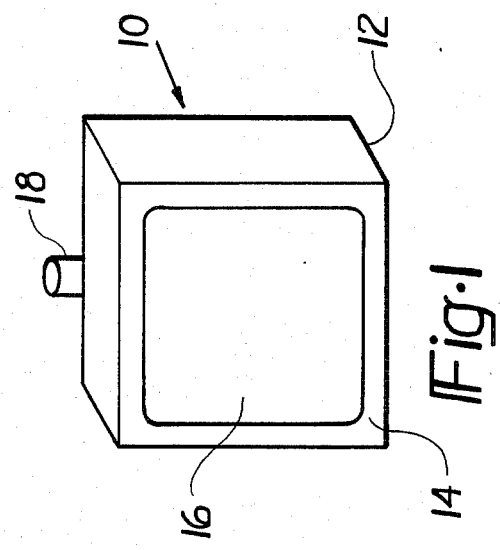
Fig·1
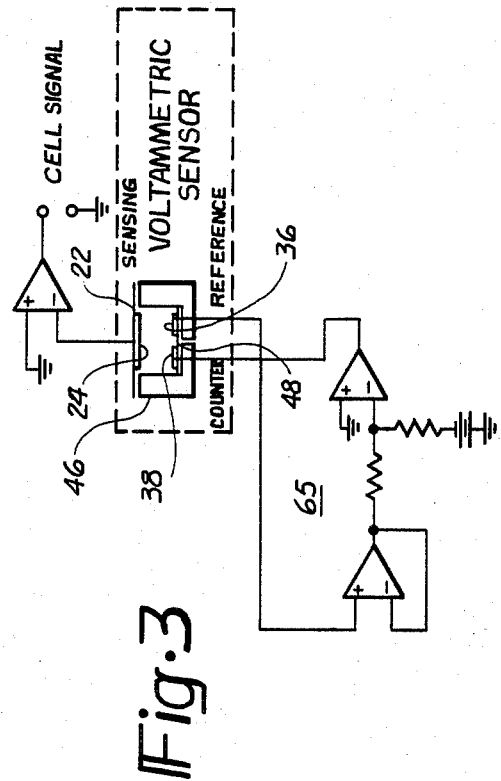
Fig·3

ENZYMATIC TOXIC GAS SENSOR

This invention relates to a detector for organophosphorous cholinesterase inhibitors, and more particularly to a miniature non-electrically powered, continuous toxic gas sensor adaptable for personal use.

PRIOR ART

Commercially available enzyme alarm and detector units weigh approximately 12.5 kg and have a volume of 24,918 cu. cm. (1,521 cu. in. or 10.6 cu. ft.). The miniature detector-alarm unit of the present invention weighs approximately 0.14 kg and has a volume of approximately 50 cu. cm. (3 cu. in.). This reduction of size, of almost three magnitudes, is due to the arrangement and use of planar sheet materials as described herein.

The prior art system, represented by Thorn Automation Limited's NAIAD system described in a 1978 brochure, is either a back-pack mounted apparatus or one mounted on a vehicle. The system contains an air pump to circulate ambient air through the detector, a liquid pump to move reagent from the reservoir to the detector wherein the ambient air, input air, is drawn in by means of the air pump. The input air is heated and its temperature is measured to ensure that the air is at the proper temperature. A separate alarm system contains the electronics necessary to respond to the detector for operating an audible means. Batteries having a life measured in hours are used to power the pumps and the detector and additional batteries power the electronics and the audible means. The detector continuously monitors the hydrolytic activity of an enzyme, cholinesterese, after exposure to an organophosphorous ester from the ambient air. The organophosphorous ester decreases the activity of the enzyme, which activity can be monitored electrically.

U.S. Pat. No. 3,451,901 entitled "Method of Detecting Nerve Gas" and issued to Seiger et al. on June 24, 1969, illustrates a detector similar to the above-described Thorn Automation Detector. The system defines the enzyme-substrate as being selected from a wide group of enzymes including AcHe. The system defines a method of detection utilizing two reservoirs one containing the enzyme and the other the substrate. An electronic motor and pump are required to mix the enzyme and the substrate then and deliver the residue to a waste reservoir. Battery power is required to operate both the detector and the alarm system.

U.S. Pat. No. 3,515,644 entitled "Reversed Enzymatic Detection Method for Anticholinesterases" and issued to Kramer et al on June 2, 1970, teaches a system for detecting G-V agents based on the deactivation of cholinesterase enzyme. The substrate is chosen to produce a noticable color when the enzyme is deactivated.

U.S. Pat. No. 4,267,023 entitled "Chemically Integrating Dosimeter and Gas Analysis Methods" and issued to Frant et al on May 12, 1981, teaches a dual membrane dosimeter to measure exposure to a gas over a long period of time.

SUMMARY OF THE INVENTION

There is disclosed and claimed herein a miniature enzymatic toxic gas sensor comprising a buffer reservoir containing a buffer solution which operates with an enzyme to maintain the enzyme in its active state. The outwardly spaced planar surface which is a porous membrane is open along its broadside to the atmosphere that may contain toxic gas. The ambient gas passes through the membrane and is exposed to an enzyme immobilized on the interior face of the membrane. The enzyme will be deactivated in the presence of certain toxic gases present in the ambient gas. The deactivation of the enzyme causes a current change which can be used to activate an alarm. In the absence of the toxic gas, the enzyme hydrolyzes a substrate that is released in a slow controlled manner from the substrate pouch. An amperometric detector is designated such that the hydrolyzed substrate, not the nonhydrolyzed substrate, is oxidized. Therefore, the amperometric current is a function of the enzymatic activity. This current will decrease upon the addition of a toxic gas, since the enzyme will be inhibited and hydrolyzed substrate will not be produced.

DETAILED DESCRIPTION OF THE DRAWINGS

In the drawings:

FIG. 1 is a perspective view of the sensor;

FIG. 2 is a schematic view of the various layers in the sensor;

FIG. 3 is a schematic of a three electrode voltammetric sensor including basic circuitry; and FIG. 4 is a schematic of an embodiment of a dual miniature enzymatic toxic gas sensor.

As illustrated in FIG. 1, the sensor 10 is a small or miniature compact unit having a solid housing 12 with one broadside 14 containing a window 16. The purpose of the window 16 is to admit ambient air into the sensor 10. As will hereinafter be explained only gases containing a cholinesterase inhibitor such as may be found in G-V agents and organophosphorous pesticides will generate an alarm from the sensor 10.

The sensor 10 illustrated in FIG. 1 weighs approximately 142 gm (5 oz) and has a size of approximately 7.6 cm×5.1 cm×1.3 cm (3"×2"×0.5"). When attached to a clip 18 or some other fastener, not shown, the sensor can be comfortably worn by an individual.

The miniature enzymatic toxic gas sensor 10 according to the present invention uses no air or liquid pumps as diffusion is adequate to transport the agent through the air to the membrane and through the liquid to the enzyme. It is well known that toxic nerve gases and organophosphorous pesticides act on the acetylcholinesterase enzyme (AcHe) in humans, therefore an agent detector, such as the sensor 10 of the present invention, which is based on the deactivation of AcHe will detect the presence of any such gas or pesticide.

Referring to FIG. 2, the sensor comprises a frame broadside member 14, a first gasket 20, a porous membrane 22 with a structure 23 containing immobilized AcHe attached to its interior face or broadside, a platinum screen sensing electrode 24, a first filter paper 26, a substrate pouch 28, a membrane support member 30, a second filter paper 32, second membrane 34 containing reference 36 and counter 38 electrodes, a PPE membrane 40, a second gasket 42 and the cell housing reservoir 44. An additional permselective membrane, not shown, may be added after the first gasket. The complete sensor 10 is packaged together between the frame broadside member 14 and the cell housing reservoir 44 and welded together forming an integral, unitary package. The sensing 24, reference 36 and counter 38 electrodes and B+ and B− are connected to electrical contacts on the membrane support member 30. Additional electrodes may be added to the sensor for temperature compensation or other features.

The basic principle of the electrical operation is illustrated in FIG. 3 which is a schematic of a three electrode voltametric sensor including an electrical circuit. The schematic illustrates a channel shaped enclosure 46 having a porous PTFE membrane 48 on the bottom inside surface. Located on the membrane are counter 38 and reference 36 cell electrode each having an electrode lead extending therefrom. Across the open end of the channel is a porous membrane 22 supporting a sensing electrode 24. In the space between the counter 38 and reference 36 cell electrode and the sensing electrode 24 is a conductive electrolyte.

The membrane 22 having one broadside adapted for interfacing with the ambient air, may be fabricated from a porous 25 micron thick polypropylene such as CELGARD 2500 membrane 22 from Celanese Plastics Co. In the alternative the membrane 22 may be fabricated from Teflon. A membrane fabricated from Teflon or polypropylene may be placed between membrane 22 and gasket 20. This membrane is impregnated with a silicon oil with a solubility parameter such that interferent gases such as HCN and $H_2S$ will not pass through, but the toxic agent will pass through. Whether or not an interferent will pass through the membrane is a function of the solubility parameter of the two materials. As a general rule, if the parameters differ by less than one unit, they will dissolve in each other.

Air in the vicinity of the sensor 10 diffuses through the porous membrane 22 containing the immobilized AcHe. The AcHe enzyme is covalenty attached to a hydrophilic support in order to stabilize the enzyme. This may be accomplished by a chemical process as described in the article written by George Baum et al in Vol 268 No. 2 (1972) pages 411-414 of *Biochimica et Biophysica Acta*, entitled "Stability, Inhibition, and Reactivation of Acetyl Cholinesterase Covalently Coupled to Glass". The end result is that the AcHe is covalently coupled to a structure 23 of commercial glass beads which are attached to the interior face or other broadside of the membrane 22.

The sensing electrode 24, comprising a fine noble metal screen such as platinum or a conductive screen coated with platinum, either being mounted on a porous membrane. In the absence of a cholinesterase inhibitor, the enzyme continuously catalyzes the hydrolysis of the substrate released from the substrate pouch 28 and the sensing electrode 24 oxidizes the hydrolyzed substrate at the sensing electrode 24. The current from this reaction is monitored by the electronic circuitry and triggers the alarm when the level of current drops below a predetermined level. In the preferred embodiment, a first filter paper 26 is placed between the sensing electrode 24 and the substrate pouch 28.

The substrate pouch 28 replaces the liquid pumps and the liquid reagent refill system of the larger prior art detectors. The main function of the substrate pouch 28 is to release the substrate in a slow controlled manner in order to prevent the current due to enzymatic hydrolysis in clean air from being inconsistent. In the preferred embodiment, the substrate pouch 28 comprises a piece of substrate-soaked filter paper 50 sandwiched between two layers 52, 54 of a polypropylene membrane one of which may be porous. The pouch 28 is ultrasonically welded completely around its perimeter.

The rate of substrate release is limited by diffusion through the porous membrane 52 which may be CELGARD 2500. The rate of diffusion is controlled by the length and diameter of the membrane pores and the relative solubility of the substrate in the pouch solvent 53 and the buffered electrolyte from the reservoir 44. In the sensor size of the preferred embodiment, the flux of the substrate is approximately $2.0 \times 10^{-8}$ moles per minute which corresponds to a three month supply of substrate at a five microamp baseline current.

The first of the three electrodes 24, 36, 38 with their associated functions is the sensing electrode 24 at which the electrochemical reactions are taking place. Its function is to quantitatively oxidize and measure the concentration of hydrolyzed substrate. The second functional electrode is the reference electrode 36. This is the electrode 36 whose potential is constant enough that it can be taken as the reference standard against which the potentials of the other electrodes in the cell can be measured. The third functional electrode is the counter electrode 38. This is the electrode that serves as a source or sink for electrons so that current can be passed through the cell.

The sensing electrode 24 cannot be combined in function with either of the others, and therefore always exists as a separate physical electrode, but the other two electrode functions can sometimes be combined so that only two physical electrodes are present in the system.

The last element in the sensor 10 is a buffer reservoir 44 containing enough solution to maintain the concentration of the substrate on the support member 30. The hydrophilic nature of the support member 30 is such that it continuously absorbs buffer from the reservoir 44 by means of the hydrophilic wick 55 shown as a broken line which is connected therebetween. The buffer in the preferred embodiment is a pH 8.9 TRIS (tris[hydroxymethyl]-aminomethane) buffer and the evaporation is such that in the size described, the buffer reservoir 44 need not be replaced more often than every six months.

The various filter papers 26, 32 function to maintain a consistent electrolyte level at electrodes. By doing so this reduces the positioning sensitivity of the electrodes in the sensor.

OPERATION

The reservoir 44 contains a buffered electrolyte such as a pH 8.9 TRIS buffer, that dissolves the substrate in the substrate poucn 28 in a slow controlled manner. The substrate is acetylthiocholine perchlorate and as it is dissolved, it diffuses through the porous membrane 52 of the pouch 28 to the immobilized enzyme on the porous membrane 22 where it is hydrolyzed generating acetic acid and thiocholine perchlorate, a mercaptan. The sensing electrode 24 is placed at a potential such that all of the released thiocholine perchlorate is oxidized but not sufficient to oxidize the nonhydrolyzed substrate. The current level is proportional to the level of hydrolyzed substrate, which is indicative of the enzymatic activity and presence of toxic gas.

When a toxic gas diffuses through the porous membrane 22 it reacts with the enzyme to inactivate the enzyme thereby reducing the hydrolysis of the substrate. This reduces the generation of thiocholine perchlorate thereby decreasing the electrochemical reaction. Less current is then generated on the sensing electrode 24. The amount of current generated on the sensing electrode 24 is inversely proportional to the amount of toxic gas present.

The reference and counter electrodes 36, 38 cooperate with the sensing electrode 24 to indicate when a predetermined level of toxic gas is present to activate a circuit means containing some form of an alarm. The circuit means 65 generates a signal of one value due to the presence of toxic gas and a signal of another value due to an absence of toxic gas.

In order to provide a long shelf life for the sensor 10 prior to use, a pin 61 and a separator 62, not shown, are positioned in the sensor. The separator 62 is positioned in the fluid path of the sensor connecting the reservoir 44 and the substrate pouch 28 to halt the flow of the buffered electrolyte through the wick 55 to the substrate pouch 28. The pin 61 is operatively connected to the reservoir 44 and the separator 62 so that upon the pin's removal from the sensor 10 the separator 62 is removed. Until the pin 61 is removed, the enzyme is dry and inactive.

One use of the sensor is in chemical warfare (CW) where toxic gases may be employed. Several toxic gases operate to inhibit enzymes such as AcHe. When such enzymes are inhibited, the electrochemical reaction taking place on the sensing electrode 24 is halted, hence no current is chemically generated. When this happens, the alarm system operatively connected to the electrodes of the sensor 10 is activated warning the wearer of the sensor 10 of the presence of toxic gas or G-V agents.

Another embodiment of the enzymatic toxic gas sensor 10 of the present invention is the combination of two of the sensors 56, 58 shown in FIG. 2 within one housing creating a dual sensor. This is schematically illustrated in FIG. 4.

In another embodiment, one of the sensors 56 is always uncovered and responds to the ambient air for the purposes of detecting toxic gases. The other sensor 58 is covered to prevent the diffusion of ambient air through the membrane 22. After detection of toxic gas, and upon the decision of the wearer of the miniature sensor, the cover 29 on the other sensor 58 may be removed and its initial response to the ambient air will be fed to the bridge circuit 60. The bridge circuit 60 includes a summing circuit, and if the toxic gas has cleared, the output of the other sensor 58 is high. This high output (current) is summed with the possible low output from the one sensor 56, due to residue of the gas on the sensing electrode therein, giving a high signal output which the alarm circuit identifies as a toxic gas clean condition.

One reason for the dual sensor is to provide compensation for the temperature drift of the uncovered sensor. A quick change in temperature will cause a signal decrease from the sensing electrode which may be interpreted as indicating the presence of toxic gas. The covered sensor will decrease equally in temperature and the summing circuit again will detect the different outputs and act accordingly.

While the sensor 10 herein has been described with respect to organophosphorous cholinesterase inhibitors, the concept is suitable to detect many different types of gases by changing the enzyme and substrate. To fabricate a personal mercury detector, cholinesterase would be replaced by yeast alcohol dehydrogenase which is inhibited by mercury. Other detectors would be fabricated to detect organophosphorous pesticides such as malathion, parathion and DDVP.

There has thus been shown and described a minature enzymatic toxic gas sensor 10 which is sensitive to cholinesterase inhibitors such as G. V. agents and organophosphorous pesticides. A long shelf life is possible due to the presence of a separator which prevents the flow of a buffered electrolyte to a substrate.

We claim:

1. A enzymatic toxic gas sensor wherein the chemical reactions therein are activated by diffusion within the sensor, said sensor comprising:
   a reservoir containing a buffered electrolyte;
   a wick attached at one end thereof to said reservoir;
   a porous membrane having one broadside adapted for interfacing with the ambient air;
   a structure attached to the other broadside of said membrane, said structure having an enzyme covalently attached thereto;
   an electrochemical cell means having a sensing electrode, a reference electrode and a counter electrode; said sensing electrode spaced from said structure and adapted to react with reaction products of said enzyme to generate an electrical current;
   substrate means adapted to receive the other end of said wick and containing a substrate which is dissolvable by said buffered electrolyte and diffuses to said enzyme to react with said enzyme in the absence of toxic gases; and
   circuit means responsive to said electrochemical cell to generate a signal of one value due to the presence of toxic gases for activating an alarm means and a signal of another value due to the absence of toxic gases.

2. A sensor according to claim 1 additionally including:
   separator means interposing said reservoir and said substrate means to prevent a reaction therebetween; and
   a pin actuation means operatively connected to said separator means for removing said separator means when said pin is removed from the sensor.

3. A gas sensor according to claim 1 wherein said structure contains acetylcholinesterase (AcHe) covalently coupled to glass beads attached to the other broadside of said membrane.

4. A gas sensor according to claim 3 wherein said alarm means is responsive to the deactivation of said acetylcholinesterase by means of a toxic gas.

5. The apparatus of claim 1 wherein said enzyme includes yeast alcohol dehydrogenase.

6. A gas sensor according to claim 1 wherein said alarm means is responsive to the deactivation of said enzyme by means of a toxic gas.

7. A dual enzymatic toxic gas sensor wherein the chemical reactions therein are activated by diffusion within the sensor, said sensor comprising:
   a first sensor having:
   a reservoir containing a buffered electrolyte;
   a wick attached at one end thereof to said reservoir;
   a porous membrane having one broadside adapted for interfacing with the ambient air;
   a structure attached to the other broadside of said membrane, said structure having an enzyme covalently attached thereto;
   an electrochemical cell means having a sensing electrode, a reference electrode and a counter electrode; said sensing electrode spaced from said structure and adapted to react with reaction products of said enzyme to generate an electrical current;
   substrate means adapted to receive the other end of said wick and containing a substrate which is dissolvable by said buffered electrolyte and diffuses to said enzyme to react with said enzyme in the absence of toxic gases;

a second sensor having:

a reservoir containing a buffered electrolyte;

a wick attached at one end thereof to said reservoir;

a porous membrane having one broadside adapted for interfacing with the ambient air;

removable cover means normally covering said one broadside from interfacing with ambient air and adaptable to be removed therefrom;

a structure attached to the other broadside of said membrane, said structure having an enzyme covalently attached thereto;

an electrochemical cell means having a sensing electrode, a reference electrode and a counting electrode; said sensing electrode spaced from said structure and adapted to react with reaction products of said enzyme to generate an electrical current;

substrate means adapted to receive the other end of said wick and containing a substrate which is dissolvable by said buffered electrolyte and diffuses to said enzyme to react with said enzyme in the absence of toxic gases; and circuit means including a bridge circuit, summing means and alarm means responsive to each of said electrochemical cells from said first and second sensors to generate a signal of one value due to the presence of toxic gases and a signal of another value due to the absence of toxic gases for activating said alarm means and responsive to the removal of said cover means to generate one of said signals in response to the electrical current from said electrochemical cell in said second sensor.

8. A sensor according to claim 7 additionally including:

separator means interposing each of said reservoir and said substrate means to prevent a reaction therebetween; and a pin actuation means operatively connected to each of said separator means for removing said separator means when said pin is removed from the sensor.

9. A gas sensor according to claim 7 wherein each of said structures contains acetylcholinesterase (AcHe) covalently coupled to glass beads attached to the other broadside of said membrane.

10. A gas sensor according to claim 9 wherein said alarm means is reponsive to the deactivation of said acetylcholinesterase by means of a toxic gas.

11. Apparatus for detecting certain toxic gases in an ambient gas comprising:

a substrate, a pouch enclosing said substrate, a pouch solvent positioned in said pouch for dissolving said substrate, said pouch including a porous membrane in a wall of said pouch, said pouch solvent and dissolved substrate positioned in contact with said porous membrane to permit said dissolved substrate to diffuse through said porous membrane, a buffered electrolyte positioned in contact with said porous membrane, whereby said substrate diffusing through said porous membrane dissolves into said electrolyte, an immobilized enzyme in contact with said buffered electrolyte to catalyze a reaction with said dissolved substrate to form reaction products, means for dissolving said toxic gases from an ambient gas into said electrolyte to permit them to inhibit said enzyme, an electrochemical cell means having a sensing electrode, a reference electrode and a counter electrode; said sensing electrode spaced from said immobilized enzyme and adapted to react with reaction products of said substrate catalyzed by said enzyme to generate an electrical current;

circuit means coupled to said electrochemical cell to generate a signal indicative at first times of an ongoing catalyzed reaction and at second times of a diminished catalyzed reaction due to an inhibited enzyme.

12. The apparatus of claim 11 wherein said porous membrane includes polypropylene.

13. The apparatus of claim 11 wherein said porous membrane includes PTFE (polytetrafluoroethylene).

14. The apparatus of claim 11 wherein said buffered electrolyte includes tris-(hydroxymethyl) aminomethane.

15. The apparatus of claim 11 further including filter paper to position said buffered electrolyte.

16. The apparatus of claim 11 wherein said substrate includes acetylthiocholine perchlorate.

17. The apparatus of claim 11 wherein said porous membrane passes by diffusion approximately $2.0 \times 10^{-8}$ moles per minute of said substrate.

18. The apparatus of claim 11 wherein said enzyme includes cholinesterase.

19. The apparatus of claim 11, wherein said enzyme includes yeast alcohol dehydrogenase.

* * * * *